United States Patent [19]
Konishi et al.

[11] 4,057,534
[45] Nov. 8, 1977

[54] METHOD FOR PREVENTING SCALE FORMATION IN A CONTINUOUS ESTER-INTERCHANGE REACTION FOR PRODUCTION OF POLYESTERS

[75] Inventors: Tadashi Konishi; Masashi Kuno, both of Matsuyama, Japan

[73] Assignee: Teijin Limited, Osaka, Japan

[21] Appl. No.: 678,390

[22] Filed: Apr. 19, 1976

[30] Foreign Application Priority Data

Apr. 23, 1975 Japan .................... 50-48570

[51] Int. Cl.$^2$ ............... C08G 63/14; C08G 63/16
[52] U.S. Cl. ..................................... 260/75 R
[58] Field of Search ..................................... 260/75 R

[56] References Cited
U.S. PATENT DOCUMENTS

| 3,511,812 | 5/1970 | Stewart et al. | 260/75 R |
| 3,634,358 | 1/1972 | Okuzumi | 260/75 R |
| 3,661,858 | 5/1972 | Gleim et al. | 260/75 R |
| 3,830,759 | 8/1974 | Barkey | 260/75 R |

Primary Examiner—Edward M. Woodberry

Attorney, Agent, or Firm—Sherman & Shalloway

[57] ABSTRACT

Scale formation in a continuous ester-interchange reaction for the production of polyesters, is prevented by subjecting a dialkyl ester of a difunctional carboxylic acid at least 80 mole% of which consists of terephthalic acid and at least one glycol to a continuous ester-interchange reaction catalyst in the presence of a catalytic amount of an ester-interchange reaction catalyst composed of a manganese compound and a lithium compound, the amount of said ester-interchange reaction catalyst being the one which meets the following expressions (i) and (ii)

(i) $0.015 < X + Y < 0.2$ (ii) $0.2 \leq Y/(X+Y) \leq 0.7$ wherein X is the amount in moles of said manganese compound based on said dialkyl ester, and Y is the amount in moles of said lithium compound based on said dialkyl ester.

8 Claims, No Drawings

METHOD FOR PREVENTING SCALE FORMATION IN A CONTINUOUS ESTER-INTERCHANGE REACTION FOR PRODUCTION OF POLYESTERS

This invention relates to an improved process for producing polyesters which comprises a continuous ester-interchange reaction in an ester-interchange reaction zone and a polycondensation reaction of the resulting ester-interchange reaction product in a polycondensation zone, wherein the improvement comprises the prevention of scale formation in the continuous ester-interchange reaction zone.

More specifically, the invention relates to a method for preventing scale formation in a continuous ester-interchange reaction for the production of polyesters, which comprises subjecting a dialkyl ester of a difunctional carboxylic acid at least 80 mole% of which consists of terephthalic acid and at least one glycol to a continuous ester-interchange reaction in the presence of a catalytic amount of an ester-interchange reaction catalyst composed of a manganese compound and a lithium compound, the amount of said ester-interchange reaction catalyst satisfying the following expressions (i) and (ii)

(i) $0.015 < X + Y < 0.2$ (ii) $0.2 \leq Y/(X + Y) \leq 0.7$ wherein X is the amount in moles of said manganese compound based on said dialkyl ester, and Y is the amount in moles of said lithium compound based on said dialkyl ester.

For example, polyethylene terephthalate is produced by subjecting a dialkyl terephthalate and ethylene glycol to an ester-interchange reaction at a temperature of about 130° to 250° C and atmospheric pressure in the presence of an ester-interchange reaction catalyst, and then polycondensing the resulting ester-interchange reaction product at about 250° to 300° C under reduced pressure. The ester-interchange reaction is carried out while removing the by-product alkanol out of the reaction system, and the polycondensation reaction is carried out while removing the by-product glycol out of the reaction system.

In order to perform the ester-interchange reaction smoothly, various metal compounds are used as a catalyst, and manganese compounds such as manganese acetate are used preferably because of their superior catalytic activity. The use of such manganese compounds, however, suffers from the defect that foreign materials are formed in the reaction system. These foreign materials adhere to the equipment, such as a reaction vessel or piping, to form scales which in turn prevent the normal operation of the equipment. Hence, the equipment must be disassembled and cleaned. Since this requires a complicated procedure, the working efficiency of the equipment is reduced. Furthermore, the adhesion of the scales gives rise to an increase in heat transmission resistance, and makes it difficult to maintain the reaction system at a predetermined temperature. These defects are very serious especially in a continuous ester-interchange reaction, and are required to be removed.

The foreign materials remain in the resulting polyester after the polycondensation reaction, and when such a polyester is melt-spun, the foreign materials present therein may cause a rise in pack pressure, and therefore, a marked shortening of the life of the spinning pack. Furthermore, when the polyester is formed into a film, the foreign materials remain in the film as fine particles, and markedly reduce its commercial value.

In order to prevent the formation of insoluble materials or scales in the continuous production of polyethylene terephthalate using a manganese compound catalyst, U.S. Pat. No. 3,391,122 (issued July 2, 1968) recommends the use of a combination catalyst composed of manganous acetate and sodium acetate. As will be shown by a comparative experiment to be given hereinbelow, the use of this combination catalyst reduces the formation of insoluble materials or scales in a continuous ester-interchange reaction as compared with the use of a manganous acetate catalyst. However, this reduction is still unsatisfactory, and a better method for preventing scale formation is desired.

We have made investigations in order to provide a satisfactory method for preventing the formation of insoluble materials or scales which cause serious troubles in the continuous ester-interchange reaction in the presence of a manganese compound catalyst for producing polyesters. As a result, we found that an ester-interchange reaction catalyst composed of a manganese compound and a lithium compound has a superior preventing effect which is of such a high degree as cannot at all be expected from the preventive effect of the combination of manganous acetate and sodium acetate.

Further investigations led to the discovery that the above superior effect can be exhibited when the total amount of the manganese compound and the lithium compound, and the ratio of the lithium compound to the total amount of the manganese compound and the lithium compound are within the specified ranges, and outside these ranges, the preventive effect is reduced fairly rapidly.

We have found that in order that the ester-interchange reaction may be catalyzed well and the formation of insoluble materials and scales may be prevented with good results, the use of a catalyst composed of a manganese compound and a lithium compound is essential, and it is further necessary that the amounts of the catalyst should meet the following expressions (i) and (ii)

(i) $0.015 < X + Y < 0.2$ (ii) $0.2 \leq Y/(X + Y) \leq 0.7$ preferably $0.3 \leq Y/(X + Y) \leq 0.5$ wherein X is the amount in moles of said manganese compound based on said dialkyl ester of a difunctional carboxylic acid, and Y is the amount in moles of said lithium compound based on said dialkyl ester of a difunctional carboxylic acid.

It is an object of this invention therefore to provide a very good method for preventing the formation of insoluble materials or scales in the continuous ester-interchange reaction for polyester production.

The above and other objects of this invention along with its advantages will become more apparent from the following description.

According to the process of this invention, an ester-interchange reaction catalyst composed of a manganese compound and a lithium compound is used when a dialkyl ester of a difunctional carboxylic acid at least 80 mole% of which consists of terephthalic acid and at least one glycol is formed by a continuous ester-interchange reaction. The catalyst must be used in the amounts which meet the above expressions (i) and (ii).

The superior improvement of the present invention cannot be achieved even if the sodium compound suggested in the above-cited U.S. Pat. No. 3,391,122 is used instead of the lithium compound in the present invention. The use of a potassium compound instead of the lithium compound can neither give rise to the superior improvement of the present invention. Furthermore, unless the amounts of the manganese compound and the lithium compound meet the above expressions (i) and (ii), even the use of the lithium compound cannot lead to the achievement of the outstanding effect in accordance with the present invention.

At least 80 mole% of the dialkyl ester of a difunctional carboxylic acid consists of a dialkyl ester of terephthalic acid, and not more than 20 mole% of the dialkyl ester may be a dialkyl ester of another difunctional carboxylic acid. Preferably, the alkyl group of the ester contains 1 to 4 carbon atoms. Examples of the other alkyl ester of difunctional carboxylic acid are alkyl esters of aromatic dicarboxylic acids such as isophthalic acid, phthalic acid or naphthalenedicarboxylic acid, aliphatic dicarboxylic acids such as adipic acid or sebacic acid, and hydroxycarboxylic acids such as 4-($\beta$-hydroxyethoxy)benzoic acid.

$C_2 - C_4$ alkylene glycols are preferred as the glycol used in the present invention. Most commonly, ethylene glycol is utilized, but a part or the whole of it may be replaced by a glycol of the formula $HO(CH_2)_nOH$ in which $n$ is 3 to 10, such as propylene glycol or tetramethylene glycol.

The manganese compound used as one component of the ester-interchange catalyst in accordance with the present invention may be any manganese compound which has an ester-interchange ability, for example, inorganic manganese compounds such as manganese halides or manganese oxide, and organic acid salts. Organic acid salts such as manganese acetate, manganese propionate, manganese salicylate, and manganese benzoate are especially preferred. The preferred amount of the manganese compound is about 0.01 to about 0.06 mole% based on the dialkyl ester of a difunctional carboxylic acid used as a raw material for polyesters. When the amount of the manganese compound used is too small, the ester-interchange reaction cannot proceed sufficiently, and when it is too large, a decomposition reaction takes place to color the resulting polyester. Accordingly, the manganese compound is desirably used in the above-specified range.

Examples of the lithium compound used together with the above manganese compound are inorganic compounds and organic acid salts of lithium, such as lithium acetate anhydride, lithium acetate dihydrate, lithium borate, lithium bromide, lithium carbonate, lithium chloride, lithium fluoride, lithium hydride, lithium hydroxide, and lithium sulfate. Particularly, from the standpoint of the solubility in the glycol component and the quality of the resulting polyester, lithium acetate anhydride, lithium acetate dihydrate, and lithium hydroxide are preferred.

The amount of the lithium compound used differs according to the amount of the manganese compound, and must meet the following expressions (i) and (ii).

(i) $0.015 < X + Y < 0.2$ (ii) $0.2 \leq Y/(X + Y) \leq 0.7$ preferably $0.3 \leq Y/(X + Y) \leq 0.5$ When the amount of the lithium compound is either too small or too large beyond the above ranges (i) and (ii), the effect of preventing the formation of insoluble substances or scales is reduced abruptly.

The manganese compound and the lithium compound may be added at any time before the completion of the ester-interchange reaction, but are added preferably before, or in the early stage, of the ester-interchange reaction. Our investigations have ascertained that the most troublesome foreign materials that form during continuous ester-interchange reaction using manganese compounds are products which result from the reaction of the terephthalic acid component and the manganese compound when the ester-interchange reaction has proceeded to a certain point, especially when the concentration of the glycol ester of terephthalic acid in the reaction system has reached at least about 60% of the entire reaction system. Preferably, therefore, the manganese compound and the lithium compound are caused to be present in the reaction system before the concentration of the glycol ester of terephthalic acid in the reaction mixture reaches the above-specified value. These compounds may be added as a mixture, or separately either simultaneously or in an optional order. For example, the manganese compound is first added, and then the ester-interchange reaction is carried out. Then, immediately before any foreign matter ascribable to the manganese compound forms during the ester-interchange reaction, the lithium compound is added.

The reaction can be carried out under any known conditions for continuous ester-interchange. For example, it can be performed at a temperature of about 140° to about 250° C and a pressure of atmospheric pressure to about 5 Kg/cm². Usually, the by-product alkanol is removed from the reaction system during the reaction.

A series of experiments were performed by the procedure described below in order to demonstrate the criticality of the essential requirement in the method of this invention, and the results are tabulated in Table 1.

A transverse cylindrical stainless steel reactor having a diameter of 20 cm and a length of 50 cm and equipped with a rectifying column and an exterior, electrically heating device, which affords a total residence amount of 2000 ml and the inside of which is divided by partitioning plates into five chambers is used, and its first chamber is charged with 825 ml/hr of molten dimethyl terephthalate and 508 ml/hr of ethylene glycol. At the same time, a mixture (a 10% by weight ethylene glycol solution) of manganese acetate tetrahydrate and lithium acetate in the proportions indicated in Table 1 are added as a catalyst continuously into the first chamber. The five chambers are heated from outside so that the temperature inside becomes 151° C in the first chamber, 172° C in a second chamber, 189° C in a third chamber, 222° C in a fourth chamber, and 255° C in a fifth chamber. Methanol that distills out is passed through the rectifying column to remove it. 45 days after the initiation of the reaction, all the reaction mixture is discharged, and the reactor is disassembled. The scales adhering to the chambers are collected, and weighed. The results are shown in Table 1.

In Comparative Runs Nos. 14 to 16, the type and amount of the catalyst are changed as shown in Table 1, and the inside temperature of the reactor is adjusted to 153° C in the first chamber, 175° C in the second chamber, 190° C in the third chamber, 225° C in the fourth chamber, and 251° C in the fifth chamber. Otherwise, the experiments are carried out in the same way as above.

The following Examples and Comparative Examples illustrate the present invention in greater details.

In these examples, all parts are by weight. The intrinsic viscosity $[\eta]$ of the polymer is determined at 30° C for a solution of the polymer in orthochlorophenol. The L and b values which represent colors are values measured by means of a Hunter colorimeter. Larger (L − b) values show better colors.

EXAMPLE 1

100 parts of dimethyl terephthalate and 70 parts of ethylene glycol were subjected to an ester-interchange reaction using 0.033 parts (0.0260 mole% based on the Table 1

| Run No. | Catalyst (Mn) Type | Amount (g/Hr) | Catalyst (Li) Type | Amount g/Hr | X + Y (mole %) | $\frac{Y}{X+Y}$ | Amount of scales deposited (g) | | | | | |
|---|---|---|---|---|---|---|---|---|---|---|---|---|
| | | | | | | | 1st chamber | 2nd chamber | 3rd chamber | 4th chamber | 5th chamber | Total |
| No. 1* | Manganese acetate | 0.356 | Lithium acetate | 0 | 0.032 | 0 | 2 | 3 | 6 | 13 | 37 | 161 |
| No. 2* | " | 0.344 | " | 0.010 | 0.034 | 0.1 | 3 | 2 | 5 | 10 | 24 | 48 |
| No. 3* | " | 0.333 | " | 0.018 | 0.036 | 0.17 | 1 | 2 | 4 | 8 | 12 | 27 |
| No. 4 | " | 0.326 | " | 0.025 | 0.038 | 0.22 | 0 | 0 | 0 | 1 | 5 | 6 |
| No. 5 | " | 0.317 | " | 0.032 | 0.039 | 0.27 | 0 | 0 | 0 | 0 | 3 | 3 |
| No. 6 | " | 0.308 | " | 0.039 | 0.041 | 0.32 | 0 | 0 | 0 | 0 | 0 | 0 |
| No. 7 | " | 0.292 | " | 0.053 | 0.044 | 0.40 | 0 | 0 | 0 | 0 | 0 | 0 |
| No. 8 | " | 0.273 | " | 0.068 | 0.047 | 0.48 | 0 | 0 | 0 | 0 | 0 | 0 |
| No. 9 | " | 0.259 | " | 0.079 | 0.050 | 0.53 | 0 | 0 | 0 | 0 | 4 | 4 |
| No. 10 | " | 0.208 | " | 0.119 | 0.058 | 0.68 | 0 | 0 | 0 | 2 | 6 | 8 |
| No. 11* | " | 0.187 | " | 0.137 | 0.062 | 0.73 | 0 | 0 | 12 | 20 | 52 | 84 |
| No. 12* | " | 0.089 | " | 0.216 | 0.080 | 0.9 | 0 | 0 | 17 | 26 | 62 | 105 |
| No. 13* | " | 0 | " | 0.287 | 0.096 | 1.0 | 0 | 0 | 32 | 41 | 80 | 153 |
| No. 14* | " | 0.292 | Sodium acetate | 0.066 | 0.044 | 0.4 | 0 | 0 | 1 | 14 | 16 | 31 |
| No. 15* | " | 0.292 | Potassium acetate | 0.079 | 0.044 | 0.4 | 1 | 7 | 10 | 19 | 40 | 77 |
| No. 16* | " | 0.292 | Calcium acetate | 0.127 | 0.044 | 0.4 | 3 | 4 | 6 | 40 | 109 | 162 |
| No. 17 | Manganese benzoate | 0.354 | Lithium acetate | 0.053 | 0.044 | 0.4 | 0 | 0 | 0 | 0 | 0 | 0 |
| No. 18 | Manganese acetate | 0.292 | Lithium hydroxide | 0.043 | 0.044 | 0.4 | 0 | 0 | 0 | 0 | 0 | 0 |

*Runs with asterisks are comparisons.
Note:
Manganese acetate is in the form of tetrahydrate, and all other compounds are anhydrous salts.

It can be seen from the results shown in Table 1 that in Runs Nos. 4 to 10, especially Runs Nos. 6 to 8, which are within the scope of the present invention, unexpectedly superior effects of improvement can be achieved than in Runs Nos. 1 to 3 and 10 to 13 which are outside the scope of the present invention and in Runs Nos. 14 to 16 in which the amounts of the catalyst components are within the scope of the present invention but the lithium compound is replaced by an analogous compound.

According to the process of this invention, the formation of insoluble substances and scales in the continuous ester-interchange reaction can be prevented to a great degree, and the reaction apparatus can be operated continuously in a stable condition over long periods of time. Hence, the working efficiency of the apparatus increases remarkably. Furthermore, the use of polyesters prepared by the process of this invention permits the life of spinning packs to be prolonged considerably at the time of melt-spinning, and fibers and films having very much reduced inclusion of foreign matter can be produced.

In the performance of the process of this invention, other ester-interchange catalysts, such as magnesium or cobalt compounds can be used so long as they do not depart from the objects of the present invention. Furthermore, any known poly-condensation catalysts can be used, and additives such as stabilizers, delusterants, color toning agents, antistatic agents, or fire retardants can be used as desired.

dimethyl terephthalate) of manganese acetate and 0.0059 parts (0.0173 mole% based on the dimethyl terephthalate) of lithium acetate anhydride as a catalyst at 150° to 240° C for 4 hours while distilling off methanol. An ethylene glycol slurry containing 0.04 part of antimony trioxide, 0.04 part of trimethyl phosphate, 0.02 part of cobalt acetate as a color toning agent and 0.5 part of titanium dioxide as a delusterant was added, and the ester-interchange reaction product was polycondensed for 4 hours in a high vacuum of less than 1 mmHg to afford polyethylene terephthalate having an intrinsic viscosity of 0.64, a softening point of 262.5° C, a color value L of 70.0, and a color value b of 3.9.

When the operation was performed continuously for 3 months under these conditions using a continuous reaction apparatus, the temperature of the heating coil of the ester-interchange tank was 235° C when the temperature of the reaction mixture was 210° C.

The resulting polyethylene terephthalate was melt-spun through a multi-holed spinneret at a rate of 80 g/min. to form 5 denier filaments. The rise of the pack pressure was as low as 0.9 to 1.2 Kg/cm²/day.

COMPARATIVE EXAMPLE 1

The continuous operation was performed for 3 months by a continuous reaction apparatus under the same conditions as in Example 1 except that lithium acetate anhydride was not added. It was necessary to adjust the temperature of the heating coil of the ester-interchange tank to 270° C. when the temperature of the reaction mixture was 210° C. The resulting polyethylene terephthalate was melt spun under the same conditions as in Example 1. The rise of the pack pressure was 5 to 6 Kg/cm$^2$/day. As compared with the case of Example 1, the heating temperature markedly rose, and it can be seen that there was considerable adhesion of foreign materials. This is also clear from the rise of the pack pressure.

COMPARATIVE EXAMPLE 2

The continuous operation was performed for 3 months using a continuous reaction apparatus under the same conditions as in Example 1 except that the amount of lithium acetate anhydride was changed to 0.05 part. It was necessary to adjust the temperature of the heating coil of the ester-interchange tank to 265° C when the temperature of the reaction mixture was 210° C. When the resulting polyethylene terephthalate was melt spun under the same conditions as in Example 1, the rise of the pack pressure was as high as 5 to 5.5 Kg/cm$^2$/day.

In comparison with Example 1, the heating temperature rose considerably, and it can be seen that the formation and deposition of foreign matter were considerable. This is also clear from the rise of the pack pressure.

COMPARATIVE EXAMPLE 3

The continuous operation was performed for 3 months by a continuous reaction apparatus under the same conditions as in Example 1 except that 0.011 part of potassium acetate was used instead of the lithium acetate anhydride. It was necessary to adjust the temperature of the heating coil of the ester-interchange tank to 275° C when the temperature of the reaction mixture was 210° C. When the resulting polyethylene terephthalate was spun under the same conditions as in Example 1, the rise of the pack pressure was as high as 7 Kg/cm$^2$/day.

In comparison with Example 1, the heating temperature rose markedly, and it can be seen that the formation and deposition of foreign matter were considerable. Furthermore, this is clear from the rise of the pack pressure.

EXAMPLE 2

The continuous operation was performed for 3 months under the same conditions as in Example 1 except that 0.0021 part of lithium hydroxide was used instead of the lithium acetate anhydride. The temperature of the heating coil of the ester-interchange tank was 237° C when the temperature of the reaction mixture was 210° C. When the resulting polyethylene terephthalate was melt spun under the same conditions as in Example 1, the rise of the pack was as small as 1.2 to 1.5 Kg/cm$^2$/day.

In comparison with Example 1, the heating temperature and the rise of the pack pressure were much the same as in Example 1, and the amount of the foreign matter formed and deposited was also much the same as in Example 1.

We claim:

1. A method for preventing scale formation in a continuous ester-interchange reaction for the production of polyesters, which comprises subjecting a dialkyl ester of a difunctional carboxylic acid at least 80 mol% of which consists of terephthalic acid and at least one glycol to a continuous ester-interchange reaction in the presence of a catalytic amount of an ester-interchange reaction catalyst composed of a manganese compound selected from the group consisting of manganese halides, manganese oxides and organic acid salts of manganese and a lithium compound selected from the group consisting of lithium acetate, lithium borate, lithium bromide, lithium carbonate, lithium chloride, lithium fluoride, lithium hydride, lithium hydroxide and lithium sulfate, the amount of said ester-interchange reaction catalyst satisfying the following expressions (i) and (ii)

(i) $0.015 < X + Y < 0.2$ (ii) $0.2 \leq Y/(X + Y) \leq 0.7$ wherein X is the amount in moles of said manganese compound based on said dialkyl ester, and Y is the amount in moles of said lithium compound based on said dialkyl ester.

2. The method of claim 1 wherein said expression (ii) is $0.3 \leq Y/(X + Y) \leq 0.5$.

3. The method of claim 1 wherein said manganese compound is an organic acid salt of manganese.

4. The method of claim 3 wherein said organic acid salt of manganese is selected from the group consisting of manganese acetate, manganese propionate, manganese salicylate and manganese benzoate.

5. The method of claim 4 wherein the amount of the manganese compound is about 0.01 to about 0.06 mole % based on the dialkyl ester of a difunctional carboxylic acid.

6. The method of claim 5 wherein the lithium compound is selected from the group consisting of lithium acetate anhydride, lithium acetate dihydrate and lithium hydroxide.

7. The method of claim 6 wherein said expression (ii) is $0.3 \leq X/(X + Y) \leq 0.5$ 8. The method of claim 1 where said glycol is at least one $C_2 - C_4$ alkylene glycol.

* * * * *